(12) United States Patent
Yoshimitsu et al.

(10) Patent No.: US 10,646,408 B2
(45) Date of Patent: *May 12, 2020

(54) DENTAL GLASS POWDER

(71) Applicant: GC Corporation, Shizuoka (JP)

(72) Inventors: Ryosuke Yoshimitsu, Tokyo (JP); Satomi Tateiwa, Tokyo (JP); Shigenori Akiyama, Tokyo (JP); Katsushi Yamamoto, Tokyo (JP); Syouichi Fukushima, Tokyo (JP)

(73) Assignee: GC CORPORATION, Shizuoka (JP)

( * ) Notice: Subject to any disclaimer, the term of this patent is extended or adjusted under 35 U.S.C. 154(b) by 93 days.

This patent is subject to a terminal disclaimer.

(21) Appl. No.: 16/086,769

(22) PCT Filed: Dec. 1, 2016

(86) PCT No.: PCT/JP2016/085805
§ 371 (c)(1),
(2) Date: Sep. 20, 2018

(87) PCT Pub. No.: WO2017/168836
PCT Pub. Date: Oct. 5, 2017

(65) Prior Publication Data
US 2019/0083364 A1    Mar. 21, 2019

(30) Foreign Application Priority Data

Mar. 28, 2016  (JP) ................. 2016-063856

(51) Int. Cl.
| A61K 6/849 | (2020.01) |
| C03C 4/00 | (2006.01) |
| C03C 3/12 | (2006.01) |
| C03C 12/00 | (2006.01) |
| C03C 3/112 | (2006.01) |
| A61K 8/02 | (2006.01) |
| A61K 8/25 | (2006.01) |
| A61K 33/16 | (2006.01) |

(52) U.S. Cl.
CPC .............. A61K 6/849 (2020.01); A61K 8/022 (2013.01); C03C 3/112 (2013.01); C03C 4/0021 (2013.01); C03C 12/00 (2013.01); A61K 8/25 (2013.01); A61K 33/16 (2013.01)

(58) Field of Classification Search
CPC .......... A61K 6/30; A61K 6/831; A61K 6/889; C03C 3/062; C03C 3/078; C03C 3/095; C03C 3/097; C03C 3/112; C03C 12/00; C03C 8/04; C03C 8/06; C03C 4/0021; C03C 4/0007
See application file for complete search history.

(56) References Cited

U.S. PATENT DOCUMENTS

| 4,775,592 | A | 10/1988 | Akahane et al. |
| 4,900,697 | A | 2/1990 | Akahane et al. |
| 5,618,763 | A | 4/1997 | Frank et al. |
| 6,217,644 | B1 | 4/2001 | Matsunae et al. |
| 6,353,039 | B1 | 3/2002 | Rheinberger et al. |
| 2002/0035025 | A1 | 3/2002 | Schweiger et al. |
| 2007/0129459 | A1 | 6/2007 | Zeng et al. |
| 2009/0208428 | A1 | 8/2009 | Hill et al. |
| 2010/0311864 | A1 | 12/2010 | Arita et al. |
| 2011/0009511 | A1 | 1/2011 | Hill et al. |
| 2014/0056954 | A1 | 2/2014 | O'Donnell et al. |
| 2019/0083364 | A1 | 3/2019 | Yoshimitsu et al. |
| 2019/0099332 | A1* | 4/2019 | Yoshimitsu ............ A61K 6/831 |
| 2019/0142702 | A1* | 5/2019 | Honda ..................... A61K 6/00 252/182.12 |
| 2019/0151204 | A1* | 5/2019 | Akiyama ............... C03C 4/0035 |

FOREIGN PATENT DOCUMENTS

| JP | S62-067008 | 3/1987 |
| JP | S63-201038 | 8/1988 |
| JP | H11-268929 | 10/1999 |
| JP | 2000-026225 | 1/2000 |
| JP | 2000-086421 | 3/2000 |
| JP | 2001-130926 | 5/2001 |
| JP | 2002-053339 | 2/2002 |
| JP | 2009-539755 | 11/2009 |
| JP | 2010-532338 | 10/2010 |
| JP | 2010-280630 | 12/2010 |
| JP | 2012-531377 | 12/2012 |
| WO | 90/015782 | 12/1990 |
| WO | 2005/074862 | 8/2005 |
| WO | 2011/000865 | 1/2011 |

OTHER PUBLICATIONS

International Search Report for PCT/JP2016/085805 dated Jan. 17, 2017.
International Search Report for PCT/JP2017/016611 dated Jun. 13, 2017.
International Search Report for PCT/JP2016/085806 dated Jan. 17, 2017.

* cited by examiner

Primary Examiner — Elizabeth A. Bolden
(74) Attorney, Agent, or Firm — IPUSA, PLLC

(57) ABSTRACT

In one aspect of the present invention, a dental glass powder contains zinc, silicon, and fluorine and does not substantially contain aluminum.

15 Claims, No Drawings

DENTAL GLASS POWDER

TECHNICAL FIELD

The present invention relates to a dental glass powder.

BACKGROUND ART

As a dental glass powder, an aluminosilicate glass powder is well known. The aluminosilicate glass powder is a glass powder containing oxides of Al (III) and Si (IV) as a main component. In particular, a fluoroaluminosilicate glass powder is widely used for a dental material because it is expected to have a tooth strengthening effect by fluorine and an effect of preventing tooth decay (see, for example, Patent Documents 1 and 2).

The fluoroaluminosilicate glass powder is known to be used for a dental glass ionomer cement.

Dental glass ionomer cement is generally composed of a fluoroaluminosilicate glass powder and a liquid containing a polycarboxylic acid-based polymer and water, and a hardened substance is obtained by an acid-base reaction of aluminum (ions) in the fluoroaluminosilicate glass powder with the polycarboxylic acid-based polymer included in the liquid.

PRIOR ART DOCUMENTS

Patent Documents

[Patent Document 1] Japanese Laid-open Patent Publication No. S62-67008
[Patent Document 2] Japanese Unexamined Patent Application Publication No. S63-201038

DISCLOSURE OF THE INVENTION

Problem to be Solved by the Invention

However, it is desired to enhance the effect of suppressing tooth demineralization.

Hence, an object in one aspect of the present invention is to provide a dental glass powder that can enhance an effect of suppressing tooth demineralization.

Means for Solving the Problem

According to one aspect of the present invention, a dental glass powder contains zinc, silicon, and fluorine and does not substantially contain aluminum.

Effects of the Invention

According to one aspect of the present invention it is possible to provide a dental glass powder that can enhance an effect of suppressing tooth demineralization.

EMBODIMENT FOR CARRYING OUT THE INVENTION

In the following, an embodiment for carrying out the present invention will be described.

<Dental Glass Powder>

A dental glass powder according to the present embodiment contains zinc, silicon, and fluorine and does not substantially contain aluminum. Thereby, it is possible to enhance the effect of suppressing tooth demineralization.

Note that in the present specification and the claim scope, not substantially containing aluminum means that the content of aluminum is less than or equal to 1% by mass in terms of aluminum oxide ($Al_2O_3$).

Even when an aluminum compound is not mixed in a material composition for a dental glass powder, this is in consideration of an aluminum compound mixed as an impurity in a producing process of the dental glass powder, a detection error of a fluorescent X-ray analyzer for evaluating a composition of the dental glass powder, and the like. Normally, unless an aluminum compound is mixed in a material for a dental glass powder, the content of aluminum in the dental glass powder does not exceed 1% by mass in terms of aluminum oxide ($Al_2O_3$).

The content of aluminum in the dental glass powder is preferably in a range of from 0% to 0.5% by mass, and is more preferably in a range of from 0% to 0.3% by mass, in terms of aluminum oxide ($Al_2O_3$).

The content of zinc in the dental glass powder is preferably in a range of from 10% to 60% by mass, and is more preferably in a range of from 20% to 55% by mass, in terms of zinc oxide (ZnO). When the content of zinc in the dental glass powder in terms of zinc oxide (ZnO) is greater than or equal to 10% by mass, the effect of suppressing tooth demineralization of the dental glass powder can be enhanced. When the content of zinc in the dental glass powder in terms of zinc oxide (ZnO) is less than or equal to 60% by mass, a glass powder having a high transparency is easily obtained.

The content of silicon in the dental glass powder is preferably in a range of from 15% to 50% by mass, and is more preferably in a range of from 20% to 40% by mass, in terms of silicon oxide ($SiO_2$). Here, silicon serves to form a network in glass. When the content of silicon in the dental glass powder in terms of silicon oxide ($SiO_2$) is greater than or equal to 15% by mass, a glass powder having a high transparency is easily obtained. When the content of silicon in the dental glass powder in terms of silicon oxide ($SiO_2$) is less than or equal to 50% by mass and is used as a glass powder for a dental cement, a dental cement having an appropriate hardening property is easily obtained.

The content of fluorine (F) in the dental glass powder is preferably in a range of from 1% to 30% by mass, and is more preferably in a range of from 3% to 20% by mass. When the content of fluorine (F) in the dental glass powder is greater than or equal to 1%, tooth can be expected to be reinforced. When the content of fluorine (F) in the dental glass powder is less than or equal to 30% by mass and is used as a glass powder for a dental cement, a dental cement having an appropriate hardening property is easily obtained.

The dental glass powder may further contain calcium, phosphorus, strontium, lanthanum, sodium, potassium, or the like.

The content of calcium in the dental glass powder is preferably in a range of from 0% to 30% by mass, and is more preferably in a range of from 5% to 20% by mass, in terms of calcium oxide (CaO). When the dental glass powder contains calcium and is used as a glass powder for a dental cement, the operability is improved.

The content of phosphorus in the dental glass powder is preferably in a range of from 0% to 10% by mass, and is more preferably in a range of from 0% to 5% by mass, in terms of phosphorus oxide (V) ($P_2O_5$). When the dental glass powder contains phosphorus and is used as a glass powder for a dental cement, the operability is improved.

The content of strontium in the dental glass powder is preferably in a range of from 0% to 40% by mass, and is more preferably in a range of from 10% to 30% by mass, in terms of strontium oxide (SrO). When the dental glass powder contains strontium and is used as a glass powder for a dental cement, the X-ray contrast property of a hardened substance of the dental cement is enhanced.

The content of lanthanum in the dental glass powder is preferably in a range of from 0% to 50% by mass, and is more preferably in a range of from 10% to 40% by mass in terms of lanthanum oxide ($La_2O_3$). When the dental glass powder contains lanthanum and is used as a glass powder for a dental cement, the resistance to acids of a hardened substance of the dental cement is enhanced.

The content of sodium in the dental glass powder is preferably in a range of from 0% to 15% by mass, and is more preferably in a range of from 1% to 10% by mass, in terms of sodium oxide ($Na_2O$). When the dental glass powder contains sodium, the refractive index of the glass powder is lowered, and the glass powder having a high transparency is easily obtained.

The content of potassium in the dental glass powder is preferably in a range of from 0% to 10% by mass, and is more preferably in a range of from 1% to 5% by mass, in terms of potassium oxide ($K_2O$). When the dental glass powder contains potassium, the refractive index of the glass powder is lowered, and the glass powder having a high transparency is easily obtained.

The dental glass powder according to the present embodiment can be applied to a dental cement such as a dental glass ionomer cement, for example.

<Method for Producing Dental Glass Powder>

A dental glass powder according to the present embodiment can be produced by, after melting a material composition containing a zinc compound, a silicon compound, and a fluorine compound and not containing an aluminum compound, pulverizing the material composition.

Examples of the zinc compound include, but are not limited to, zinc oxide, zinc fluoride, and the like, and two or more kinds may be used in combination as the zinc compound.

Examples of the silicon compound include, but are not limited to, anhydrous silicic acid and the like, and two or more kinds may be used in combination as the silicon compound.

Examples of the fluorine compound include, but are not limited to, calcium fluoride, strontium fluoride, sodium fluoride, and the like, and two or more kinds may be used in combination as the fluorine compound.

The material composition may further contain a compound such as a calcium compound, a phosphorus compound, a strontium compound, a lanthanum compound, a sodium compound, and a potassium compound.

Examples of the calcium compound include, but are not limited to, calcium fluoride, calcium phosphate, calcium carbonate, calcium hydroxide and the like, and two or more kinds may be used in combination as the calcium compound.

Examples of the phosphorus compound include, but are not limited to, calcium phosphate, strontium phosphate, sodium dihydrogenphosphate, and the like, and two or more kinds may be used in combination as the phosphorus compound.

Examples of the strontium compound include, but are not limited to, strontium fluoride, strontium hydroxide, strontium carbonate, strontium oxide, strontium phosphate, and the like, and two or more kinds may be used in combination as the strontium compound.

Examples of the lanthanum compound include, but are not limited to, lanthanum fluoride, lanthanum oxide, and the like, and two or more kinds may be used in combination as the lanthanum compound.

Examples of the sodium compound include, but are not limited to, sodium dihydrogenphosphate, sodium carbonate, sodium fluoride, and the like, and two or more kinds may be used in combination as the sodium compound.

Examples of the potassium compound include, but are not limited to, potassium fluoride, potassium carbonate, potassium hydrogencarbonate, dipotassium hydrogen phosphate, and the like, and two or more kinds may be used in combination as the potassium compound.

Note that each compound in the material composition may be mixed in accordance with a composition of the dental glass powder other than aluminum.

The number average particle diameter of the dental glass powder according to the present embodiment is preferably in a range of from 0.02 µm to 30 µm, and is more preferably in a range of from 0.02 µm to 20 µm. When the dental glass powder whose number average particle diameter is greater than or equal to 0.02 µm is used as a glass powder for a dental cement, the operability is improved. When the number average particle diameter of the dental glass powder is less than or equal to 30 µm, the wear resistance of a hardened substance of a dental cement is enhanced.

<Dental Glass Ionomer Cement>

A dental glass ionomer cement according to the present embodiment includes a dental glass powder according to the present embodiment.

Under the presence of water, due to an acid-base reaction of zinc (ions) in the dental glass powder with a polycarboxylic acid-based polymer, the dental glass powder according to the present embodiment is hardened.

Examples of the polycarboxylic acid-based polymer include, but are not limited to, a homopolymer or copolymer of an α,β-unsaturated carboxylic acid.

Examples of the α,β-unsaturated carboxylic acid include acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, and the like.

Also, the polycarboxylic acid-based polymer may be a copolymer of an α,β-unsaturated carboxylic acid and a component that is copolymerizable with the α,β-unsaturated carboxylic acid.

Examples of the component that is copolymerizable with an α,β-unsaturated carboxylic acid include acrylamide, acrylonitrile, a methacrylic ester, acrylates, vinyl chloride, allyl chloride, vinyl acetate, and the like.

In this case, the proportion of the α,β-unsaturated carboxylic acid to the monomer constituting the polycarboxylic acid-based polymer is preferably greater than or equal to 50% by mass.

Among these polycarboxylic acid-based polymers, a homopolymer or copolymer of acrylic acid or itaconic acid is particularly preferable.

Usually, the dental glass ionomer cement further includes a liquid containing a polycarboxylic acid-based polymer and water, and the dental glass powder and the liquid containing the polycarboxylic acid-based polymer and water are mixed and then kneaded to prepare a kneaded substance of the dental glass ionomer cement for use.

Note that at least part of the polycarboxylic acid-based polymer may be a powder.

The mass ratio of the dental glass powder to the liquid when preparing the kneaded substance of the dental glass ionomer cement is preferably between 1 and 5. When the mass ratio of the dental glass powder to the liquid is greater than or equal to 1, the strength of a hardened substance of the dental glass ionomer cement can be enhanced. When the mass ratio of the dental glass powder to the liquid is less than or equal to 5, the viscosity of the kneaded substance of the dental glass ionomer cement is appropriate and a kneading operation of the dental glass powder and the liquid is easy.

EXAMPLES

In the following, the present invention will be described in detail with reference to Examples and Comparative Examples. Note that the present invention is not limited to the examples.

Examples 1 to 8

After zinc oxide (ZnO), anhydrous silicic acid ($SiO_2$), calcium fluoride ($CaF_2$), calcium phosphate ($Ca_3(PO_4)_2$), strontium fluoride ($SrF_2$), phosphorus oxide ($P_2O_5$), lanthanum oxide ($La_2O_3$), sodium fluoride (NaF), and potassium hydrogen carbonate ($KHCO_3$) were mixed at a predetermined ratio, and the mixture was sufficiently mixed and stirred using a mortar. The obtained mixture was placed in a platinum crucible, and it was placed in an electric furnace. The electric furnace was heated to 1300° C., and the mixture was melted and sufficiently homogenized. Subsequently, the mixture was poured into water to obtain aggregated glass. Using a ball mill made of alumina, the obtained aggregated glass was pulverized for 20 hours and then it was caused to pass through a sieve of 120 meshes to obtain glass powder.

Note that although an aluminum compound was not mixed in the material composition in Examples 1 to 8, 0.1% to 0.5% by mass of aluminum was detected in terms of aluminum oxide ($Al_2O_3$). A possible cause of this is that alumina derived from a ball made of alumina a pot made of alumina used at the time of pulverization was mixed or a detection error of a fluorescent X-ray analyzer.

Comparative Examples 1 to 6

After zinc oxide (ZnO), aluminum oxide ($Al_2O_3$), aluminum fluoride ($AlF_3$), anhydrous silicic acid ($SiO_2$), calcium fluoride ($CaF_2$), calcium phosphate ($Ca_3(PO_4)_2$), strontium fluoride ($SrF_2$), phosphorus oxide ($P_2O_5$), lanthanum oxide ($La_2O_3$), sodium fluoride (NaF), and potassium hydrogen carbonate ($KHCO_3$) were mixed at a predetermined ratio, and the mixture was sufficiently mixed and stirred using a mortar. The obtained mixture was placed in a platinum crucible, and it was placed in an electric furnace. The electric furnace was heated to 1300° C., and the mixture was melted and sufficiently homogenized. Subsequently, the mixture was poured into water to obtain aggregated glass. Using a ball mill made of alumina, the obtained aggregated glass was pulverized for 20 hours and then it was caused to pass through a sieve of 120 meshes to obtain glass powder.

Next, the number average particle diameters and the compositions of the glass powders were evaluated.

<Number Average Particle Diameter of Glass Powder>

The particle size distributions of the glass powders were measured using a laser diffraction scattering type particle size distribution analyzer LA-950 (manufactured by HORIBA, Ltd.) As a result, in each of the glass powders of Examples and Comparative Examples, the number average particle diameter was in a range of from 6 μm to 9 μm.

<Composition of Glass Powder>

Using a fluorescent X-ray analyzer ZSX Primus II (manufactured by Rigaku Corporation), the glass powders were analyzed to find their compositions.

Table 1 indicates the compositions of the glass powders (unit: mass %).

Note that the contents of Zn, Al, Si, Ca, P, Sr, La, Na, and K are respectively the contents in terms of ZnO, $Al_2O_3$, $SiO_2$, CaO, $P_2O_5$, SrO, $La_2O_3$, $Na_2O$, and $K_2O$.

Next, the effect of suppressing tooth demineralization and the hardening property of each glass ionomer cement were evaluated.

<Preparation of Kneaded Substance of Glass Ionomer Cement>

The glass powder and a 50% by mass aqueous solution of polyacrylic acid were mixed such that the mass ratio of the glass powder to the 50% by mass aqueous solution of polyacrylic acid was 1.8 and then kneaded to obtain a kneaded substance of the glass ionomer cement.

<Effect of Suppressing Tooth Demineralization>

While water was poured, bovine dentine was polished by #1200 water-resistant abrasive paper. To the flat polished surface, a polytetrafluoroethylene seal, having a hole of which diameter is 3 mm, was attached. The kneaded substance of the glass ionomer cement was applied to half of the face of the hole, and it was left to stand in a thermostatic chamber at 37° C. and 100% RH for 24 hours to harden the kneaded substance of the glass ionomer cement.

The bovine dentin, on which the hardened substance was formed, was immersed in a demineralized liquid (50 mM of acetic acid, 1.5 mM of calcium chloride, 0.9 mM of potassium dihydrogen phosphate, pH 4.5) at 37° C. for 24 hours. The other half of the face of the hole, in contact with the demineralized liquid and on which the hardened substance was not formed, was tested as a test surface.

Using a precision cutting machine, the bovine dentin, on which the hardened substance was formed, was cut such that the thickness became 1 mm, and a test object was obtained.

Using an X-ray inspection apparatus, the test object was photographed by a transmission method. Using image processing software, the photographed image was analyzed to find the amount of mineral loss and to evaluate the effect of suppressing tooth demineralization. The criteria for determining the effects of suppressing tooth demineralization are as follows. Note that as the value of the amount of mineral loss decreases, the effect of suppressing tooth demineralization increases.

A: When the amount of mineral loss is less than 2100 volume %·μm

B: When the amount of mineral loss is greater than or equal to 2100 volume %·μm and less than 2600 volume %·μm C: When the amount of mineral loss is greater than or equal to 2600 volume %·μm Here, the effect of suppressing tooth demineralization was evaluated in a manner similar to that described above except that the kneaded substance of the dental cement was not applied at all. As a result, the amount of mineral loss was greater than or equal to 4557 vol %·μm.

<Hardening Property>

A mold (8 mm×75 mm×100 mm) adjusted to be at 23° C. was placed on an aluminum foil, and the mold was filled with the kneaded substance of the glass ionomer cement up to the height of the upper surface of the mold. 60 seconds after the end of kneading, the kneaded substance of the glass ionomer cement was left to stand in a thermostatic chamber at 37° C. and 100% RH to harden the kneaded substance of the glass ionomer cement. 90 seconds after the end of kneading, 400 g of a Vicat needle was lowered vertically onto the surface of the hardened substance and it was maintained for 5 seconds. This operation was performed at intervals of 10 seconds to find the time until the dent by the Vicat needle became not a perfect circle (see ISO 9917-1 Water-based cements Part1: Powder/liquid acid-base cements 8.1 Net setting time). Note that the criteria for determining the hardening properties are as follows.

A: When the hardening time is greater than or equal to 1 minute 30 seconds and less than or equal to 6 minutes B: When the hardening time is greater than 6 minutes seconds or less than 1 minute 30 seconds Table 1 indicates the evaluation results of the effects of suppressing tooth demineralization and the hardening properties of the glass ionomer cements.

TABLE 1

COMPOSITION UNIT/MASS %

| | Example | | | | | | | | Comparative Example | | | | | |
|---|---|---|---|---|---|---|---|---|---|---|---|---|---|---|
| | 1 | 2 | 3 | 4 | 5 | 6 | 7 | 8 | 1 | 2 | 3 | 4 | 5 | 6 |
| Zn | 50.5 | 30.0 | 26.4 | 23.8 | 45.0 | 49.5 | 41.7 | 25.2 | | | | 4.6 | | |
| F | 3.0 | 5.2 | 6.5 | 6.8 | 3.3 | 3.2 | 4.7 | 5.8 | 13.5 | 13.1 | 12.0 | 11.2 | 9.4 | 13.2 |
| Al | 0.3 | 0.3 | 0.3 | 0.5 | 0.3 | 0.1 | 0.3 | 0.2 | 25.9 | 23.9 | 25.9 | 21.3 | 21.4 | 25.5 |
| Si | 33.0 | 22.9 | 24.7 | 23.1 | 35.5 | 34.8 | 37.7 | 26.8 | 23.8 | 24.0 | 25.1 | 23.6 | 20.9 | 23.3 |
| Ca | 13.2 | 7.1 | 9.6 | 9.3 | 11.4 | | 12.1 | 6.6 | | 0.3 | 0.1 | 1.8 | | |
| P | | | | 4.5 | | | | | 1.3 | 4.6 | 3.5 | 3.5 | 1.0 | 4.4 |
| Sr | | | | | | 12.4 | | | 35.5 | 34.1 | 31.9 | 28.0 | 47.3 | 21.5 |
| La | | 34.5 | 32.5 | 36.5 | | | | 33.2 | | | | 6.0 | | 4.6 |
| Na | | | | | | | 3.5 | | | | | 1.5 | | 3.2 |
| K | | | | | | | | 2.2 | | | | | | 4.3 |
| TOTAL | 100.0 | 100.0 | 100.0 | 100.0 | 100.0 | 100.0 | 100.0 | 100.0 | 100.0 | 100.0 | 100.0 | 100.0 | 100.0 | 100.0 |
| EFFECT OF SUPPRESSING TOOTH DEMINERALIZATION | A | A | A | B | A | A | A | A | C | C | C | C | C | C |
| AMOUNT OF MINERAL LOSS [VOLUME % · μm] | 1401 | 1951 | 1927 | 2106 | 1657 | 1878 | 1724 | 1901 | 2615 | 2888 | 2931 | 3072 | 2893 | 2777 |
| HARDENING PROPERTY | A | A | A | A | A | A | A | A | A | A | A | A | A | A |

As can been seen from Table 1, the glass ionomer cements including the glass powders of Examples 1 to 8 have a large effect of suppressing tooth demineralization.

In contrast, the glass ionomer cements including the glass powders of Comparative Examples 1 to 6 have a low effect of suppressing tooth demineralization because the content of aluminum in the glass powders is between 21.3% and 25.9% by mass in terms of aluminum oxide ($Al_2O_3$).

The present international application is based upon and claims the benefit of priority of Japanese Patent Application No. 2016-063856, filed on Mar. 28, 2016. The entire contents of Japanese Patent Application No. 2016-063856 are hereby incorporated herein by reference.

The invention claimed is:

1. A dental glass powder comprising zinc, silicon, and fluorine and not substantially comprising aluminum,
   wherein a content of zinc in the glass powder in terms of zinc oxide (ZnO) is greater than or equal to 10% by mass and less than or equal to 60% by mass,
   wherein a content of silicon in the glass powder in terms of silicon oxide ($SiO_2$) is greater than or equal to 15% by mass and less than or equal to 50% by mass, and
   wherein a content of fluorine (F) in the glass powder is greater than or equal to 1% by mass and less than or equal to 30% by mass.

2. The dental glass powder according to claim 1, wherein the content of zinc in the glass powder in terms of zinc oxide (ZnO) is greater than or equal to 20% by mass.

3. The dental glass powder according to claim 1, wherein the content of zinc in the glass powder in terms of zinc oxide (ZnO) is less than or equal to 55% by mass.

4. The dental glass powder according to claim 1, wherein the content of fluorine (F) in the glass powder is greater than or equal to 3% by mass.

5. The dental glass powder according to claim 1, wherein the content of fluorine (F) in the glass powder is less than or equal to 20% by mass.

6. The dental glass powder according to claim 1, wherein the content of silicon in the glass powder in terms of silicon oxide ($SiO_2$) is greater than or equal to 20% by mass and less than or equal to 40% by mass.

7. The dental glass powder according to claim 1, further comprising:
   calcium,
   wherein a content of calcium in the glass powder in terms of calcium oxide (CaO) is greater than or equal to 5% and less than or equal to 20% by mass.

8. The dental glass powder according to claim 1, further comprising:
   strontium,
   wherein a content of strontium in the glass powder in terms of strontium oxide (SrO) is greater than or equal to 10% by mass and less than or equal to 30% by mass.

9. The dental glass powder according to claim 1, further comprising:
   phosphorus,
   wherein a content of phosphorus in the glass powder in terms of phosphorus oxide (V) ($P_2O_5$) is less than or equal to 5% by mass.

10. The dental glass powder according to claim 1, further comprising:
   lanthanum,
      wherein a content of lanthanum in the glass powder in terms of lanthanum oxide ($La_2O_3$) is greater than or equal to 10% by mass and less than or equal to 40% by mass.

11. The dental glass powder according to claim 1, further comprising:
   sodium,
      wherein, a content of sodium in the glass powder in terms of sodium oxide ($Na_2O$) is greater than or equal to 1% by mass and less than or equal to 10% by mass.

12. The dental glass powder according to claim 1, further comprising:
   potassium,
      wherein a content of potassium in the glass powder in terms of potassium oxide ($K_2O$) is preferably greater than or equal to 1% by mass and less than or equal to 5% by mass.

13. The dental glass powder according to claim 1, further comprising:
   calcium or lanthanum.

14. The dental glass powder according to claim 1, wherein the content of fluorine (F) in the glass powder is less than or equal to 6.8% by mass.

15. The dental glass powder according to claim 1, further comprising:
   strontium,
      wherein a content of strontium in the glass powder in terms of strontium oxide (SrO) is less than or equal to 12.4% by mass.

* * * * *